United States Patent [19]

Labroo et al.

[11] Patent Number: 5,939,385
[45] Date of Patent: Aug. 17, 1999

[54] TRANSGLUTAMINASE CROSS-LINKABLE POLYPEPTIDES AND METHODS RELATING THERETO

[75] Inventors: Virender Labroo, Mill Creek; Sharon J. Busby, Seattle, both of Wash.

[73] Assignee: ZymoGenetics, Inc., Seattle, Wash.

[21] Appl. No.: 08/483,236

[22] Filed: Jun. 7, 1995

Related U.S. Application Data

[63] Continuation of application No. 08/106,509, Aug. 13, 1993, Pat. No. 5,428,014.

[51] Int. Cl.[6] ................................................ A61K 38/00
[52] U.S. Cl. .............................. 514/12; 514/13; 514/14; 514/15; 514/16; 514/21
[58] Field of Search .................... 514/12, 21, 13, 514/14, 15, 16

[56] References Cited

U.S. PATENT DOCUMENTS 4,589,882  5/1986  Urry ........................................ 530/330

FOREIGN PATENT DOCUMENTS 4347162  2/1992  Japan.

OTHER PUBLICATIONS

Melham, "Elastic Fiber Assembly: Macromolecular Interactions" Caplus 1996:372833, 1995.

*Primary Examiner*—Cecilia J. Tsang
*Assistant Examiner*—Patrick R. Delaney
*Attorney, Agent, or Firm*—Paul G. Lunn, Esq.; Roberta A. Picard; Gary E. Parker

[57] ABSTRACT

Polypeptides of from about 9–120 amino acid residues comprising a truncated segment of fibrinogen which may be flanked by elastomeric peptides, wherein the polypeptides are cross-linkable by a transglutaminase, homo- and copolymers containing such polypeptides are disclosed. The homo- and co-polymers disclosed herein are useful in tissue sealant and wound healing formulations.

54 Claims, No Drawings

TRANSGLUTAMINASE CROSS-LINKABLE POLYPEPTIDES AND METHODS RELATING THERETO

RELATED CASES

The present application is a continuation of Ser. No. 08,/106,509, filed Aug. 13, 1993, which application has been allowed as U.S. Pat. No. 5,428,014, and which is incorporated herein by reference.

BACKGROUND OF THE INVENTION

Biocompatible polymeric materials are used for a number of medical applications. For example, biocompatible synthetic polymers such as expanded polytetrafluorethylene and polyethyleneterephthalate (e.g., DACRON) are used to construct vascular grafts. A wide variety of biodegradable polymers are combined with drugs and formed into microspheres and other structures to provide implantable devices for timed-release drug delivery. Biodegradable polymers are also used for sutures, surgical screws, plates and pins that are widely used in surgery, including orthopedic surgery.

Naturally occurring polymers, such as proteins, are also used medically. For example, fibrinogen-based tissue adhesives are used to control bleeding and to reattach or reconstruct severed or damaged tissue. These adhesives are used alone or in conjunction with mechanical fasteners such as sutures or staples. Although a number of fibrinogen-based tissue adhesives have been reported (see, for review, Sierra, *J. Biomat. Appl.* 7: 309–352, 1993), their use has been limited by the need to extract fibrinogen from plasma, which carries a risk of disease transmission, and by the problems related to the purity of the bovine thrombin used as the clotting catalyst in some of the current products. Bovine thrombin preparations are extremely impure, and are suspected of being immunogenic (Strickler et al., *Blood* 72: 1375–1380, 1988; Zehnder et al., *Blood* 76: 2011–2016, 1990; Lawson et al., *Blood* 76: 2249–2257, 1990). Antibodies elicited by the bovine thrombin preparations interact with human proteins and leave the patient's clotting system impaired. To date, the production of recombinant fibrinogen in commercial quantities has not been reported.

Elastomeric polypeptides have been disclosed, for example, in U.S. Pat. Nos. 4,500,700; 4,870,055; and 4,187,852. These patents disclose small synthetic polypeptides that may be polymerized to produce insoluble cross-linked elastomeric fibers or cellophane-like sheets. U.S. Pat. Nos. 4,132,746; 4,187,852; 4,870,055; and 4,589,882 disclose methods of producing randomly cross-linked elastomeric copolymers using enzymatic, chemical or γ-radiation induced cross-linking. PCT publication WO 88/03533 discloses polyoligomers of repeating, relatively short, amino acid sequence units. The polyoligomers are produced by recombinant DNA methodology, and are exemplified by silk-like proteins. WO 90/05177 discloses similar polyoligomers wherein strands of repeating units capable of assembling into aligned structures are interspersed with unaligned oligopeptides. While these polymers provide structural matrices, they are not bioadhesive and are not suitable for in vivo use. While, as discussed above, methods of producing cross-linked polymers have been disclosed, the methods may be inappropriate for in vivo use due to the toxicity of the cross-linking agent or the rate of cross-linking.

There remains a need in the art for biomaterials that can be polymerized into homo- and copolymers that are capable of forming stable matrices of aligned structures that are cross-linked in a chemically defined manner. There is a further need for matrices capable of adhering to animal tissue to facilitate surgical sealing, as well as subsequent wound healing and tissue restructuring. There is also a need for tissue adhesives that do not contain blood-derived components. There is an additional need for biomaterials whose physical properties can be altered by adjusting environmental parameters, such as pH, temperature, or ionic strength, allowing them to be formed in situ. The present invention provides such materials as well as other, related advantages.

SUMMARY OF THE INVENTION

It is an object of the present invention to provide transglutaminase cross-linkable polypeptides that can be polymerized into biocompatible homopolymers or copolymers and that undergo a conformational transition in response to environmental change. It is a further object of the invention to provide cross-linkable biocompatible materials that can be used to produce tissue adhesives, wound repair formulations, rigid prosthetic devices, matrices for the replacement or repair of bone or soft tissue structure and as carriers for controlled drug release compositions. In one embodiment, the present invention provides a polypeptide of from about 9–120 amino acid residues comprising a segment of the formula $S_1$-Y-$S_2$, wherein: $S_1$ is selected from the group consisting of Ile-Gly-Glu-Gly-Gln (SEQ ID NO:1), Gly-Glu-Gly-Gln (SEQ ID NO:2), Glu-Gly-Gln (SEQ ID NO:3), and Gly-Gln (SEQ ID NO:4); Y is His-His-Leu-Gly-Gly (SEQ ID NO:5) or His-His-Leu-Gly (SEQ ID NO:6); and $S_2$ is selected from the group consisting of Ala-Lys-Gln-Ala-Gly-Asp (SEQ ID NO:7), Ala-Lys-Gln-Ala-Gly (SEQ ID NO:8), Ala-Lys-Gln-Ala (SEQ ID NO:9), Ala-Lys-Gln (SEQ ID NO:10), Ala-Lys-Ala-Gly-Asp-Val (SEQ ID NO:11), Ala-Lys-Ala (SEQ ID NO:12) and Ala-Lys (SEQ ID NO:13), wherein said polypeptide has an amino-terminus and a carboxy-terminus and is cross-linkable by a transglutaminase. A preferred polypeptide is Gly-Gln-His-His-Leu-Gly-Gly-Ala-Lys-Gln (SEQ ID NO:14). In another embodiment, a preferred transglutaminase is Factor XIII.

The invention also provides a polypeptide wherein the polypeptide is flanked on either or both the amino-terminus and the carboxy-terminus by an elastomeric polypeptide. The invention further provides an elastomeric polypeptide wherein the elastomeric polypeptide is a pentapeptide or a tetrapeptide. In a particularly preferred aspect, the invention provides a flanked polypeptide wherein the flanking elastomeric polypeptide is Val-Pro-Gly-Val-Gly (SEQ ID NO:15), Ala-Pro-Gly-Val-Gly (SEQ ID NO:16), Gly-Val-Gly-Val-Pro (SEQ ID NO:17), Val-Pro-Gly-Gly (SEQ ID NO:18) or any portion thereof, preferably such that the amino-terminus of the flanked polypeptide is Val and the carboxy-terminus of the flanked polypeptide is Gly. As will be evident to one skilled in the art, the amino acid residues referred to throughout this application, except as noted, utilize the generally accepted three-letter code. Also provided by the present invention are high molecular weight, soluble, transglutaminase cross-linkable homo- and copolymers.

The present invention further provides biocompatible polymers that are cross-linkable by a transglutaminase and that are additionally bioadhesive. An advantage of the present invention is that the transglutaminase cross-linkable polypeptides can be used in a variety of homo- and copolymer formulations which can be cross-linked by a transglutaminase to add stability to the biomaterial and will enable the biomaterial to adhere to tissue surfaces.

In a related aspect, the present invention provides biocompatible, bioadhesive, transglutaminase cross-linkable copolymers which comprise: a) a first polypeptide monomer wherein said first polypeptide monomer comprises a polypeptide of from about 9–120 amino acid residues comprising a segment of the formula $S_1$-Y-$S_2$, wherein: $S_1$ is selected from the group consisting of Ile-Gly-Glu-Gly-Gln (SEQ ID NO:1), Gly-Glu-Gly-Gln (SEQ ID NO:2), Glu-Gly-Gln (SEQ ID NO:3), and Gly-Gln (SEQ ID NO:4); Y is His-His-Leu-Gly-Gly (SEQ ID NO:5) or His-His-Leu-Gly (SEQ ID NO:6); and $S_2$ is selected from the group consisting of Ala-Lys-Gln-Ala-Gly-Asp (SEQ ID NO:7), Ala-Lys-Gln-Ala-Gly (SEQ ID NO:8), Ala-Lys-Gln-Ala (SEQ ID NO:9), Ala-Lys-Gln (SEQ ID NO:10), Ala-Lys-Ala-Gly-Asp-Val (SEQ ID NO:11), Ala-Lys-Ala (SEQ ID NO:12) and Ala-Lys (SEQ ID NO:13), wherein the first polypeptide monomer has an amino-terminus and a carboxy-terminus and is cross-linkable by a transglutaminase; and b) a second polypeptide monomer comprising a polypeptide capable of being non-enzymatically polymerized into soluble, biocompatible, bioadhesive polymers. A preferred transglutaminase is Factor XIII.

In one aspect the invention provides a copolymer comprising a first polypeptide monomer wherein the first polypeptide monomer is flanked on either or both the amino-terminus and the carboxy-terminus by an elastomeric polypeptide. The invention further provides an elastomeric polypeptide wherein the elastomeric polypeptide is a pentapeptide or a tetrapeptide. In a particularly preferred embodiment, the invention provides a flanked first polypeptide monomer wherein the flanking elastomeric polypeptide is Val-Pro-Gly-Val-Gly (SEQ ID NO:15), Ala-Pro-Gly-Val-Gly (SEQ ID NO:16), Gly-Val-Gly-Val-Pro (SEQ ID NO:17), Val-Pro-Gly-Gly (SEQ ID NO:18) or any portion thereof, preferably such that the resultant amino-terminus of the flanked first polypeptide monomer is Val and the carboxy-terminus of the flanked first polypeptide monomer is Gly. Within another aspect of the invention the second polypeptide monomer of the copolymer comprises a polypeptide capable of being non-enzymatically polymerized with the first polypeptide monomer, forming a soluble, bioadhesive, biocompatible copolymer. Such second polypeptide monomers include polypeptides of the formula: Val-Pro-Gly-Val-Gly (SEQ ID NO:15), Ala-Pro-Gly-Val-Gly (SEQ ID NO:16), Gly Val Gly Val Pro (SEQ ID NO:17), and Val-Pro-Gly-Gly (SEQ ID NO:18).

In a related aspect, the present invention provides biocompatible, transglutaminase cross-linkable homopolymers which comprise polypeptide monomers selected from the group consisting o from about 9–120 amino acid residues comprising a segment of the formula $S_1$-Y-$S_2$, wherein: $S_1$ is selected from the group consisting of Ile-Gly-Glu-Gly-Gln (SEQ ID NO:1), Gly-Glu-Gly-Gln (SEQ ID NO:2), Glu-Gly-Gln (SEQ ID NO:3), and Gly-Gln (SEQ ID NO:4); Y is His-His-Leu-Gly-Gly (SEQ ID NO:5) or His-His-Leu-Gly (SEQ ID NO:6); and $S_2$ is selected from the group consisting of Ala-Lys-Gln-Ala-Gly-Asp (SEQ ID NO:7), Ala-Lys-Gln-Ala-Gly (SEQ ID NO:8), Ala-Lys-Gln-Ala (SEQ ID NO:9), Ala-Lys-Gln (SEQ ID NO:10), Ala-Lys-Ala-Gly-Asp-Val (SEQ ID NO:11), Ala-Lys-Ala (SEQ ID NO:12) and Ala-Lys (SEQ ID NO:13) wherein said polypeptide monomer has an amino-terminus and a carboxy terminus and is cross-linkable by a transglutaminase. In another embodiment, a preferred transglutaminase is Factor XIII.

In one aspect the invention provides a polypeptide monomer wherein the polypeptide monomer is flanked on either or both the amino-terminus and the carboxy-terminus by an elastomeric polypeptide. The invention further provides an elastomeric polypeptide wherein the elastomeric polypeptide is a pentapeptide or a tetrapeptide. In a particularly preferred aspect the invention provides flanked polypeptide monomers wherein the flanking elastomeric polypeptide is Val-Pro-Gly-Val-Gly (SEQ ID NO:15), Ala-Pro-Gly-Val-Gly (SEQ ID NO:16), Gly-Val-Gly-Val-Pro (SEQ ID NO:17), Val-Pro-Gly-Gly (SEQ ID NO:18) or any portion thereof, preferably such that the resultant amino-terminus of the flanked polypeptide monomer is Val and the carboxy-terminus of the flanked polypeptide monomer is Gly.

The present invention further provides tissue adhesive kits comprising: a first container containing a homo- or copolymer of the present invention; and a second container containing an activated transglutaminase. Within another aspect, the present invention provides tissue adhesive kits comprising: a first container containing a non-activated transglutaminase and a homo- or copolymer of the present invention; and a second container containing a transglutaminase activator. Within these aspects of the invention, the kits may further comprise an applicator. Within a related aspect the contents of the kits of the present invention are in the form of a lyophilized powders and/or a concentrated liquid and wherein the kits further comprise a third container containing a physiologically acceptable diluent. Within other aspects of the invention, the tissue adhesive kits contain factor XIII as the transglutaminase. Within certain aspects of the invention, the transglutaminase is activated by thrombin.

These and other aspects of the invention will become evident upon reference to the following detailed description.

DETAILED DESCRIPTION OF THE INVENTION

As noted above, the present invention is directed to polypeptides that can be polymerized, or can be copolymerized with other polypeptides, to provide biocompatible, bioadhesive homo- or copolymers. The resulting polymers can be cross-linked by a transglutaminase to produce a stabilized matrix. These homo- and copolymers can be used as components of tissue adhesives, for producing prosthetic or other devices for implantation into the body (see, for example, Urry, PCT publication WO 89/10100; which is incorporated by reference herein in its entirety), for the production of matrices for the replacement or repair of bone or soft tissue structure (see, for example, Urry, PCT Publication WO 89/1099, which is incorporated by reference herein in its entirety) and as carriers for the production of controlled drug delivery devices (see, for example, Urry, EP 449 592). As will be evident to one skilled in the art, polypeptides represent a union of two or more amino acids joined by peptide bonds and bounded by free amino and carboxyl-termini.

As used herein, the term "polymer" refers to a substance containing two or more polypeptide monomers. The term "homopolymer" refers to polymers containing two or more identical polypeptide monomers. The term "copolymer" includes any polymer containing two or more types of polypeptide monomers.

Biocompatible polymers are those polymers that, when implanted into a living animal, are non-toxic, do not elicit a foreign body or inflammatory response that causes the implant to be physically rejected from the surrounding tissue and which are broken down by natural processes in vivo into non-toxic products. Within the present invention, it is desirable that the homo- and copolymers be degraded and eliminated from the body within one to twelve weeks, preferably within two to six weeks.

The term "bioadhesive" refers to the ability of polymers to adhere to animal tissue. Bioadhesive strength can be measured by determining the shear adhesive strength of the polymer using methods described, for example, by Sierra et al. (*Larynaoscope* 100: 360–363, 1990) and Sierra et al. (*J. Appl. Biomat.* 3: 147–151, 1992), which are incorporated herein by reference in their entirety. In an exemplary assay, skin from white pigs is obtained, and split thickness skin (0.44 mm) is harvested with an electric dermatome (Paget, Kansas City, Mo.). Stainless steel jigs are glued to the epidermal surface of the harvested skin with cyanoacrylate adhesive (e.g., WONDER BOND PLUS, Borden, Inc. Columbus, OH, or the like), and the skin is trimmed to fit the jigs (cross-sectional area of 625 mm$^2$). The test adhesive is applied to the dermal surface of the lower jig, then the upper jig is placed on the test adhesive such that the test adhesive is sandwiched between the skin layered on the jigs. Fibrin sealant, made by mixing human fibrinogen (Enzyme Research Laboratories, Inc.) and bovine thrombin (Armour Pharmaceutical Co., Tarrytown, N.Y.), is used as an adhesive standard. The jigs are incubated in a moist chamber at 35° C. for a time sufficient to allow the adhesive to set, approximately twenty minutes. The jigs are then attached to a 100 Newton load cell of a materials tester (Instron, Canton, Mass.), and the jigs are pulled apart at a rate of 5 mm/min. Data is collected at a rate of 50 points/second. Stress at peak load is determined and expressed in kPa (kiloPascals). Suitable bioadhesives will exhibit between 1 kPa and 35 kPa, preferably between 1 and 20 kPa, in this assay.

Transglutaminases catalyze the cross-linking of proteins via the formation of $\epsilon$-($\gamma$-glutamyl)lysine isopeptide bonds between protein-bound glutamine and lysine residues. The formation of the isopeptide bond is preceded by the formation of a thiolester intermediate between the glutamine residue and the enzyme. The thiolester intermediate is susceptible to hydrolysis by water. The reaction of the thiolester intermediate with water instead of the amine donor group of lysine causes the thiolester intermediate to hydrolize to a glutamic acid residue instead of forming a glutamine-lysine isopeptide bond. Thus the susceptibility of a cross-linking site to deamidation will reduce the production of isopeptide cross-links and will therefore compromise dimer formation.

Polypeptides that are cross-linkable by transglutaminases can be obtained from proteins that have been demonstrated to be transglutaminase substrates (for review see McDonagh, *Hemostasis and Thrombosis*, Colman et al., Eds., J. B. Lipincott & Co., Philadelphia, 1987) such as from portions of the gamma chain of fibrinogen, $\beta$-casein, fibronectin, myosin, actin, factor V (Francis et al., *J. Biol. Chem.* 261: 9787–9792, 1986) thrombospondin, lipoprotein (a), $\alpha$2-plasmin inhibitor (Ichinose et al., *FEBS Lett.* 153: 369–371, 1983), $\alpha_2$-macroglobulin and collagen (Mosher et al., *J. Biol. Chem.* 255: 1181–1188, 1990). In a preferred embodiment, the cross-linkable polypeptide is derived from the fibrinogen gamma chain. However, as will be appreciated by those skilled in the art, suitable polypeptides can be obtained from any protein that can be cross-linked to itself, to other proteins and/or to living tissue by a transglutaminase. See, for example, Lorand and Conrad, *Mol. Cell. Biochem.* 58: 9–35, 1984; and McDonagh, in *Hemostasis and Thrombosis: Basic Principles and Clinical Practice*, 2nd. ed. Colman et al., eds. J. B. Lipincott & Co., Philadelphia, 1987, which are incorporated herein by reference.

The present invention provides polypeptides of from 3–120 amino acid residues comprising a segment of the formula Gln-Y-Lys, wherein Y is a spacer peptide of 1 to 12 amino acids, wherein said polypeptides are cross-linkable by a transglutaminase.

In a preferred embodiment, the present invention provides a polypeptide of from about 9–120 amino acid residues comprising a segment of the formula $S_1$-Y-$S_2$, wherein: $S_1$ is selected from the group consisting of Ile-Gly-Glu-Gly-Gln (SEQ ID NO:1), Gly-Glu-Gly-Gln (SEQ ID NO:2), Glu-Gly-Gln (SEQ ID NO:3), and Gly-Gln (SEQ ID NO:4); Y is His-His-Leu-Gly-Gly (SEQ ID NO:5) or His-His-Leu-Gly (SEQ ID NO:6); and $S_2$ is selected from the group consisting of Ala-Lys-Gln-Ala-Gly-Asp (SEQ ID NO:7), Ala-Lys-Gln-Ala-Gly (SEQ ID NO:8), Ala-Lys-Gln-Ala (SEQ ID NO:9), Ala-Lys-Gln (SEQ ID NO:10), Ala-Lys-Ala-Gly-Asp-Val (SEQ ID NO:11), Ala-Lys-Ala (SEQ ID NO:12) and Ala-Lys (SEQ ID NO:13), wherein the polypeptide has an amino-terminus and a carboxy-terminus and is cross-linkable by a transglutaminase. In a particularly preferred embodiment, the polypeptide is Gly-Gln-His-His-Leu-Gly-Gly-Ala-Lys-Gln (SEQ ID NO:14).

The polypeptides of the present invention can be chemically synthesized according to conventional procedures, such as by the solid-phase method of Barany and Merrifield (in *The Peptides. Analysis, Synthesis, Biology* Vol. 2, Gross and Meienhofer, eds, Academic Press, NY, pp. 1–284, 1980) either manually or by use of an automated peptide synthesizer. The polypeptides can also be synthesized by conventional solution phase methodology. The polypeptides are then screened for the ability to form transglutaminase-induced cross-links using methods described in more detail below. As will be evident to one skilled in the art, polypeptides can be prepared in which the sequence and content of the spacer and flanking sequences can be altered by deletion, addition or replacement to improve the cross-linking rate and/or to reduce the deamidation of the intermediate. For example, the spacer sequence from Gln, amino acid 7, to Gly, amino acid 12, in the polypeptide sequence Thr-Ile-Gly-Glu-Gly-Gln-Gln-His-His-Leu-Gly-Gly-Ala-Lys-Gln-Ala-Gly-Asp-Val can be reduced by deletion of one or all of the amino acid residues. In a like manner, the amino-terminus sequences flanking Gln, amino acid residue 6, and the carboxy-terminus sequences flanking Lys, amino acid residue 14, can be deleted to shorten the polypeptide.

Polypeptides are screened for the ability to form transglutaminase-catalyzed cross-links using a cross-linking assay as described in more detail below. Briefly, reaction tubes are prepared in which approximately 0.5 mg of each lyophilized test polypeptide substrate is dissolved in 50 mM Tris, 125 mM NaCl (pH 7.6) to a final concentration of 2 mM by weight. Where necessary, the pH of the solution is adjusted to 7.6 with 0.1N NaOH. Each reaction receives 50 mM CaCl$_2$ to a final concentration of 2.5 mM. A negative control for each test substrate is also prepared in which the reaction lacks a transglutaminase (e.g., Factor XIII). A positive control of the fibrinogen polypeptide (The-Ile-Gly-Glu-Gly-Gln-Gln-His-His-Leu-Gly-Ala-Lys-Gln-Ala-Gly-Asp-Val) is used for each set of reactions. The reactions are initiated by the addition of 40 $\mu$g/ml of transglutaminase (e.g., recombinant Factor XIII) followed by 0.1 unit of bovine thrombin (Enzyme Research Laboratories, Inc., South Bend, Ind.) to each solution, except the negative controls. The reactions are incubated in a 37° C. water bath. A time course of 10 $\mu$l samples are taken from each reaction at 0 minutes, 30 minutes, 60 minutes, 120 minutes and overnight. The reactions are stopped by boiling for one minute. After the reactions are terminated, each sample is diluted to 50 $\mu$l with 40 $\mu$l of TBS buffer (120 mM NaCl, 50 mM Tris (pH 7.6)) and the samples are prepared for HPLC analysis.

Each sample is chromatographed on a C-18 reverse phase HPLC column (Vydac, Hesperia, Calif. or the like) using a gradient of 0–40% B in 30 minutes (Solvent A: 0.05% trifluoroacetic acid (TFA) in water and Solvent B: 0.045% TFA in 80% acetonitrile, 20% water) on a Hewlett Packard 1090 Series II HPLC or the like. The signal is detected at a wavelength of 215 nm. The area % of each reaction product is collected and plotted versus time to determine the rates of polypeptide utilization dimer formation and multimer formation. A deamidation ratio is determined by dividing the deamidation rate by the dimerization rate. Suitable polypeptides exhibit at least the same rate of substrate utilization, dimer formation and deamidation ratio as the fibrinogen polypeptide control.

The overnight sample from each reaction was subjected to HPLC-Mass Spectroscopy using a PE SCIEX API III system (Perkin Elmer Sciex Instruments, Thornhill, Ontario, Canada) in combination with a Waters 625 LC (Waters Chromatography, Milford, Mass.) system equipped with an autosampler to identify the molecular masses of the species present in each reaction.

The overnight samples prepared as described above were collected and arranged into batches. Each batch of samples was preceded by a 0.1M acetic acid indicator sample and followed by the fibrinogen peptide control. The batches were chromatographed on a C-18 reverse phase column (2.1×150 mm, 5$\mu$, 300 angstrom; Vydac, Hesperia, Calif., or the like) using a gradient of 0–50% B in 30 minutes (solvent A: 0.05% TFA in water and Solvent B: 0.045% TFA in 80% acetonitrile/20% water) on the Waters LC (Waters Chromatography, Milford, Mass.) system equipped with an autosampler programmed to deliver 20 $\mu$l of each sample. The flow from the HPLC was split approximately 10:1 via the SCIEX splitter with the smaller volume being directed (at approximately 20 $\mu$l/min) into the mass analyzer and the remainder of the flow directed back to the HPLC UV detector in the Waters LC. This arrangement created a short, consistent (approximately 0.3 min) delay between the mass determination and the UV absorbance detection due to the length of the path traveled by the flow to the UV detector. The signal was detected by the UV detector at a wavelength of 215 nm. The molecular mass of each component in each HPLC peak was determined by the PE SCIEX API III Mass Analyzer (IonSpray source with triple quaprapole resolution) that had been calibrated with a polypropylene glycol mw 1000 solution (Aldrich Chemical Company Inc., Milwaukee, Wis.) designating the following m/z (mass to charge ratios):

59.000
520.395
906.673
1254.92
1545.133
1836.342
2010.468

The PE SCIEX API III was programmed to the following parameters:

| DACs SETTINGS | |
|---|---|
| ISV | 5500.00 |
| IN | 650.00 |
| OR | 65.00 |
| RO | 30.00 |
| M1 | 1000.00 |
| RE1 | 120.00 |
| DM1 | 0.09 |
| R1 | 27.00 |
| L7 | −50.00 |
| R2 | −50.00 |
| M3 | 1000.00 |
| RE3 | 122.00 |
| DM3 | 0.09 |
| R3 | −75.00 |
| L9 | −250.00 |
| FP | −250.00 |
| MU | −4200.00 |

| On/Offs SETTINGS | |
|---|---|
| CC | 1 |
| CG | Off |

| ADCs SETTINGS | |
|---|---|
| DI$\mu$A | −0.20 |
| CGT | −1.53 |
| ISv | 4.89 |
| UV | −24.43 |

The mass data generated from each peak was interpreted to identify the molecular species present from each peak. As would be evident to one skilled in the art the parameters provided above are brand and machine specific and as such particular parameters for each machine must be derived in a brand and machine-specific manner.

In the alternative, pools of DNA sequences encoding candidate polypeptides can be generated by known methods, such as saturation mutagenesis (Little, *Gene* 88: 113–115, 1990; Hermes et al., *Gene* 88: 143–151, 1989), by segment-directed mutagenesis (Shortle et al., *Proc. Natl. Acad. Sci. USA* 77: 5375–5379, 1980) or by forced nucleotide misincorporation (Liao and Wise, *Gene* 88: 107–111, 1990) of a DNA sequence encoding the polypeptide of interest. Pools of DNA sequences encoding candidate polypeptides can also be generated by synthesizing randomly mutagenized oligonucleotides using, for example, the method described by Hutchinson et al. (*Proc. Natl. Acad. Sci. USA* 83: 710–714, 1986). The pools of candidate polypeptides can then be expressed in an appropriate host cell, purified and screened as described above.

As noted above, within one embodiment of the invention, copolymers of a first polypeptide monomer comprising a polypeptide that is cross-linkable by a transglutaminase and a second polypeptide monomer comprising a polypeptide capable of being non-enzymatically polymerized into soluble, biocompatible, bioadhesive polymers are disclosed. Polypeptides suitable for use as second polypeptide monomers can be derived from structural proteins having desirable physical characteristics. Preferred physical characteristics include the ability to bind tissue and the ability to form fibers. Suitable proteins in this regard include elastin, tropoelastin, collagen, silk, loricrin (Hohl et al., *J. Biol. Chem.* 266: 6626–6636, 1991), involucrin (*Cell* 46: 583–589, 1986 and Etoh et al., *Biochem. Biophys. Res. Comm.* 136: 51–56, 1986) fibronectin (for review see Yamada, *Current Opinion in Cell Biology* 1: 956–963, 1989; Sekiguchi et al., *Proc. Natl. Acad. Sci. USA* 77: 2661–2665, 1980), thrombospondin (Zardi et al., *EMBO J.* 6: 2337–3342, 1987; Gutman and Kornblihtt, *Proc. Natl. Acad. Sci. USA* 84: 7179–7182, 1987). Certain proteins, such as involucrin, collagen and silk have repeat peptide sequences that can be used as second polypeptide monomers within the polymers of the present invention. Preferred polypeptides include elastomeric polypeptides disclosed by Urry and Okamoto (U.S. Pat. Nos. 4,132,746 and 4,187,852; which are incorporated by reference herein in their entirety), Urry (U.S. Pat. Nos. 4,474,851; 4,500,700; and 5,064,430; which are incorporated by reference herein in their entirety) and Urry and Prasad (U.S. Pat. Nos. 4,783,523 and 4,970,055; which are incorporated by reference herein in their entirety). In this regard, polypeptides of the formulas Val-Pro-Gly-Val-Gly (SEQ ID NO: 15), Ala-Pro-Gly-Val-Gly (SEQ ID NO:16), Gly Val Gly Val Pro (SEQ ID NO:17) and Val-Pro-Gly-Gly (SEQ ID NO:18) are preferred. As will be evident to one skilled in the art, the adhesiveness of the copolymers may be increased by the incorporation of adhesive sequences into the second polypeptide monomer. Adhesive sequences can be obtained from any protein containing tissue-binding domains and include integrin binding sequences such as Arg-Gly-Asp. The copolymers of the present invention may also include additional types of polypeptide monomers that confer desirable physical characteristics to the copolymer such as increased tissue adhesion, increased tensile strength and/or increased elasticity. Within one embodiment of the invention, the copolymers include 1–6 additional types of polypeptide monomers. Such additional polypeptide monomers are different than the first and second polypeptide monomers, although they may confer similar characteristics.

Further provided by the invention is a cross-linkable polypeptide having an amino-terminus and a carboxy-terminus wherein the cross-linkable polypeptide is flanked on either or both the amino terminus and the carboxy terminus by an elastomeric polypeptide. The invention further provides an elastomeric polypeptide wherein the elastomeric polypeptide is a pentapeptide or a tetrapeptide. Flanked cross-linkable polypeptides wherein the flanking elastomeric polypeptide is Val-Pro-Gly-Val-Gly (SEQ ID NO:15), Ala-Pro-Gly-Val-Gly (SEQ ID NO:16), Gly-Val-Gly-Val-Pro (SEQ ID NO:17), Val-Pro-Gly-Gly (SEQ ID NO:18) or any portion thereof, preferably such that the resultant amino-terminus of the flanked cross-linkable polypeptide is Val and the carboxy-terminus of the flanked cross-linkable polypeptide is Gly are particularly preferred.

The polypeptides of the present invention can be synthesized by solid phase or solution phase methods conventionally used for the synthesis of polypeptides (see, for example, Merrifield, R. B. *J. Amer. Chem. Soc.* 85: 2149–2154, 1963; Birr, C. *Aspects of the Memfield Peptide Synthesis*, Springer-Verlag, Heidelberg, 1978; Carpino, L.A., *Acc. Chem. Res.* 6: 191–198, 1973; Kent S. B., *Ann. Rev. Biochem.* 57: 957–989, 1988; Gregg et al. *Int. J. Peptide Protein Res.* 35: 161–214, 1990; *The Peptides. Analysis, Synthesis, Biology*, Vol. 1, 2, 3, 5: Gross, E and Meinhofer, J. eds., Acad. Press, New York, 1979; Stewart et al., *Solid Phase Peptide Synthesis*, 2nd. ed. Pierce Chem. Co., Rockford, IL, 1984; which are incorporated herein by reference in their entirety.) The use of solid phase methodology is preferred. Briefly, an N-protected C-terminus amino acid residue is linked to an insoluble support such as divinylbenzene cross-linked polystyrene, polyacrylamide resin, Kieselguhr/polyamide (pepsyn K), controlled pore glass, cellulose, polypropylene membranes, acrylic acid-coated polyethylene rods or the like. Cycles of deprotection, neutralization (in the case of BOC chemistry, vide infra) and coupling of successive protected amino acid derivatives are used to link the amino acids from the Carboxy-terminus according to the amino acid sequence. Preferred solid supports are divinylbenzene cross-linked polystyrene resins, which are commercially available in a variety of functionalized forms, including chloromethyl resin, hydroxymethyl resin, paraacetamidomethyl resin, benzhydryl amine (BHA) resin, p-methylbenzhydrylamine (MBHA) resin, oxime resins, 4-alkoxybenzyl alcohol resin, 4-(2',4'-dimethoxyphenylaminomethyl)-phenoxymethyl resin, 2,4-dimethoxybenzhydrylamine resin, and 4-(2', 4'-dimethoxyphenyl-FMOC-aminomethyl)-phenoxyacetamidonorleucyl-MBHA resin (Rink amide MBHA resin). A preferred protecting group for the α-amino group of the amino acids is acid-labile t-butyloxycarbonyl (BOC). BOC is deprotected using trifluoroacetic acid (TFA) in a suitable solvent, such as methylene chloride. The resultant TFA salt is neutralized with a base, such as diisopropylethyl amine (DIEA) or triethylamine ($Et_3N$), then coupled with the protected amino acid derivative. Another preferred protecting group for α-amino acids is base-labile 9-fluorenylmethoxycarbonyl (FMOC). Suitable protecting groups for the side chain functionalities of amino acids chemically compatible with BOC and FMOC groups are well known in the art. FMOC-amino acid-WANG resins are commercially available from, for example Nova Biochem (as Calbiochem, La Jolla, Calif.) and Advanced ChemTech (Louisville, Ky.) among others. The amino acid residues can be coupled by using a variety of coupling agents and chemistries known in the art, such as direct coupling with DIC (diisopropylcarbodiimide), DCC or BOP; via preformed symmetrical anhydrides; via active esters such as pentafluorophenyl esters; or via pre-formed hydroxlybenztriazole active esters (HOBt). Activation with DIC in the presence of HOBt is preferred.

The solid phase method can be carried out manually, although automated synthesis on a commercially available peptide synthesizer (e.g. Applied Biosystems 431A, Advanced ChemTech 200, or the like) or multiple peptide synthesizer (Advanced ChemTech, Louisville Ky., or the like) is preferred. In a typical synthesis using an Advanced ChemTech synthesizer, FMOC-amino acid-WANG resin is treated with 20% piperidine in dimethylformamide (DMF) to remove the FMOC group. After washing the resin with DMF, the second amino acid is coupled using the DIC/HOBt method. Successive deprotection (with 20% piperidine) and coupling cycles are used to build the whole polypeptide sequence. Alternatively, the carboxyl terminus FMOC-amino acid residue may be loaded on the Wang resin by different methods such as by DIC/DMAP (diisopropylcarbodiimide/dimethylaminopyridine) or by the protocol available with the Applied Biosystems synthesizers. As will be evident to one skilled in the art, synthesis methods may vary according to the automated synthesizer used and suitable synthesis protocols will generally be supplied by the manufacturer. The choice of a suitable synthesis method is well within the level of ordinary skill in the art.

After synthesis, the polypeptides are deprotected by piperidine and cleaved with a TFA solution(0.25 ml $H_2O$, 0.25 ml ethanedithiol, 9.5 ml TFA). Alternatively, the cleavage can be carried out with Reagent K (0.75 g crystalline phenol, 0.25 ml ethanedithiol, 0.5 ml thioanisole, 0.5 ml deionized water, 10 ml TFA) or the like. The polypeptides are isolated by first precipitating and washing with ether followed by purification by reverse phase HPLC and characterized by amino acid analysis and mass spectroscopy. It may be preferable to include non-natural amino acids, such as D-amino acids within the polypeptides of the present invention to increase the half-life of the formulations.

As will be evident to one skilled in the art, the polypeptides and polymers of the present invention can also be produced in genetically engineered host cells according to conventional techniques. DNA sequences encoding the polypeptides and polymers of the present invention can be obtained from genomic and/or cDNA clones or can be synthesized de novo according to conventional procedures. Suitable host cells are those cell types that can be transformed or transfected with exogenous DNA and grown in culture, and include bacteria, fungal cells, and cultured higher eukaryotic cells. Techniques for manipulating DNA molecules and introducing exogenous DNA into a variety of host cells are disclosed by Sambrook et al., *Molecular Cloning: A Laboratory Manual,* 2nd ed., Cold Spring Harbor Laboratory Press, Cold Spring Harbor, N.Y., 1989, which is incorporated herein by reference.

In general, DNA sequences encoding the polypeptides described herein are operably linked to transcription promoters and terminators within suitable expression vectors. Expression vectors for use in the present invention will commonly contain one or more selectable markers and one or more origins of replication, although those skilled in the art will recognize that within certain systems selectable markers can be provided on separate vectors, and replication of the exogenous DNA can be provided by integration into the host cell genome. Selection of promoters, terminators, selectable markers, vectors and other elements is a matter of routine design within the level of ordinary skill in the art. Many such elements are described in the literature and are available through commercial suppliers.

To direct polypeptides of the present invention into the secretory pathway of the host cells, a secretory signal sequence (also known as a leader sequence, prepro sequence or pre sequence) is provided in the expression vector. The secretory signal sequence is joined to the DNA sequence encoding the polypeptide of interest in the correct reading frame. Secretory signal sequences are commonly positioned 5' to the DNA sequence encoding the protein of interest, although certain signal sequences can be positioned 3' to the DNA sequence of interest (see, e.g., Welch et al., U.S. Pat. No. 5,037,743; Holland et al., U.S. Pat. No. 5,143,830).

Yeast cells, particularly cells of the genus Saccharomyces, are a particularly preferred host for use within the present invention. Methods for transforming yeast cells with exogenous DNA and producing recombinant proteins therefrom are disclosed by, for example, Kawasaki, U.S. Pat. No. 4,599,311; Kawasaki et al., U.S. Pat. No. 4,931,373; Brake, U.S. Pat. No. 4,870,008; Welch et al., U.S. Pat. No. 5,037, 743; and Murray et al., U.S. Pat. No. 4,845,075, which are incorporated herein by reference. A preferred vector system for use in yeast is the POT1 vector system disclosed by Kawasaki et al. (U.S. Pat. No. 4,931,373), which allows transformed cells to be selected by growth in glucose-containing media. Transformation systems for other yeasts, including *Hansenula polymorpha, Schizosaccharomyces pombe, Kluyveromyces lactis, Kluyveromyces fragilis, Ustilago maydis, Pichia pastoris, Pichia guillermondil* and *Candida maltosa* are known in the art. See, for example, Gleeson et al., *J. Gen. Microbiol.* 132: 3459–3465, 1986 and Cregg, U.S. Pat. No. 4,882,279.

Other fungal cells are also suitable as host cells. For example, Aspergillus cells can be utilized according to the methods of McKnight et al., U.S. Pat. No. 4,935,349, which is incorporated herein by reference. Methods for transforming *Acremonium chrysogenum* are disclosed by Sumino et al., U.S. Pat. No. 5,162,228, which is incorporated herein by reference.

Cultured mammalian cells can also be used as hosts. Methods for introducing exogenous DNA into mammalian host cells include calcium phosphate-mediated transfection (Wigler et al., *Cell* 14: 725, 1978; Corsaro and Pearson, *Somatic Cell Genetics* 7: 603, 1981: Graham and Van der Eb, *Virology* 52: 456, 1973), electroporation (Neumann et al., *EMBO J.* 1: 841–845, 1982) and DEAE-dextran mediated transfection (Ausubel et al., eds., *Current Protocols in Molecular Biology,* John Wiley and Sons, Inc., N.Y., 1987), which are incorporated herein by reference. The production of recombinant proteins in cultured mammalian cells is disclosed, for example, by Levinson et al., U.S. Pat. No. 4,713,339; Hagen et al., U.S. Pat. No. 4,784,950; Palmiter et al., U.S. Pat. No. 4,579,821; and Ringold, U.S. Pat. No. 4,656,134, which are incorporated herein by reference. Preferred cultured mammalian cells include the COS-1 (ATCC No. CRL 1650), COS-7 (ATCC No. CRL 1651), BHK (ATCC No. CRL 1632), BHK 570 (ATCC No. CRL 10314) and 293 (ATCC No. CRL 1573; Graham et al., *J. Gen. Virol.* 36: 59–72, 1977) cell lines. Additional suitable cell lines are known in the art and available from public depositories such as the American Type Culture Collection, 12301 Parklawn Dr., Rockville, Md.

Other higher eukaryotic cells can also be used as hosts, including insect cells, plant cells and avian cells. Transformation of insect cells and production of foreign proteins therein is disclosed by Guarino et al., U.S. Pat. No. 5,162, 222 and Bang et al., U.S. Pat. No. 4,775,624, which are incorporated herein by reference. The use of *Agrobacterium rhizogenes* as a vector for expressing genes in plant cells has been reviewed by Sinkar et al., *J. Biosci. (Bangalore)* 11: 47–58, 1987.

Preferred prokaryotic host cells for use in carrying out the present invention are strains of the bacteria *Escherichia coli,* although Bacillus and other genera are also useful. Techniques for transforming these hosts and expressing foreign DNA sequences cloned therein are well known in the art (see, e.g., Sambrook et al., ibid.).

Transformed or transfected host cells are cultured according to conventional procedures in a culture medium containing nutrients and other components required for the growth of the chosen host cells. A variety of suitable media, including defined media and complex media, are known in the art and generally include a carbon source, a nitrogen source, essential amino acids, vitamins and minerals. Media can also contain such components as growth factors or serum, as required. The growth medium will generally select for cells containing the exogenously added DNA by, for example, drug selection or deficiency in an essential nutrient which is complemented by the selectable marker carried on the expression vector or co-transfected into the host cell.

The polypeptides of the present invention can be purified by first isolating the polypeptides from the cells followed by conventional purification such as by ion-exchange and partition chromatography as described by, for example, Coy et al. (Peptides Structure and Function, Pierce Chemical Company, Rockford, Ill., pp 369–372, 1983), by reverse-phase chromatography as described, for example, by Andreu and Merrifield (*Eur. J. Biochem.* 164: 585–590, 1987), or by HPLC as described, for example, by Kofod et al. (*Int. J. Peptide and Protein Res.* 32: 436–440, 1988). Additional purification can be achieved by conventional chemical purification means, such as liquid chromatography, gradient centrifugation, and gel electrophoresis, among others. Methods of protein purification are known in the art (see generally, Scopes, R., *Protein Purification,* Springer-Verlag, N.Y. 1982, which is incorporated by reference herein) and can be applied to the purification of the recombinant polypeptides described herein.

Methods for polymerization of the polypeptides of the present invention will be evident to one skilled in the art. Techniques for polymerization of polypeptides have been described by, for example, Li and Yamashiro, *J. Amer. Chem. Soc.* 92: 7608–7609, 1970; which is incorporated herein in its entirety). The homo- and copolymers of the present invention can be synthesized sequentially in an automatic peptide synthesizer or by polymerizing activated polypeptide monomers. Polypeptide monomers with protected side chains prepared by solid or solution phase methodology can be polymerized by the same activating procedures used in peptide synthesis, such as carbodiimide-mediated coupling; pre-formed active ester (such as ONP-(paranitrophenyl ester) activated esters); BOP (benzotriazolyl N-oxytrisdimethylaminophosphonium hexafluorophosphate), PyBOP (benzotriazole-1-yl-oxy-tris-pyrrolidino phosphonium hexafluorophosphate), PyBrOP (bromo-tris-pyrrolidino-phosphonium hexafluorophosphate) or HBTU ([2-(1H-Benzotriazole-1-yl),1,1,3,3-tetramethyluronium hexafluorophosphate])-mediated coupling with or without HOBt; or variations and improvements thereof known in the art (see, for example, Coste et al., *Tetrahedron Lett.* 31: 669, 1990 and Coste et al., *Tetrahedron Lett.* 31: 205, 1990). Coupling can be done manually or by automated means. In a preferred embodiment, coupling is achieved by carbodiimide-mediated coupling using EDCI and HOBt. The polymerization of polypetide monomers into homo- or copolymers can be achieved using a shear stirring technique to orient the linear elastomeric units and 1-(3-dimethylaminopropyl)-3-ethylcarbodiimide hydrochloride (EDCI) as described by Urry et al. (U.S. Pat. No. 4,870,055, which is incorporated by reference herein). It may be preferable to use long reaction times and replenishment of EDCI to obtain the polymers. Particularly preferred polymers having molecular weights greater than 10,000 daltons, preferably up to 100,000 daltons.

Within one embodiment, the polymers are prepared with the ratio of first polypeptide monomers: second polypeptide monomers of 0.1–0.3:1.0 being more preferable. A ratio of first polypeptide monomers: second polypeptide monomers of about 0.2:1.0 being most preferred. As will be evident to one skilled in the art, the degree of cross-linking can be varied to provide the desired mechanical properties (such as flexibility and tensile strength) by altering the monomer ratio. As such, the particular ratios will vary according to the material characteristic desired from the polymer. In the case of polymers containing more than two types of polypeptide monomer, the monomer ratio will also vary according to the desired characteristics desired. For example, an elastomeric transglutaminase-cross-linkable copolymer with increased tissue binding ability may be obtained by polymerizing polypeptide monomers with a higher ratio of tissue binding monomers relative to the other monomers present.

The polymers of the present invention have the property of coacervation, in which the polymer undergoes a concentration-dependent phase separation that can be catalyzed by alterations in pH, ionic strength, cation concentration or temperature. The conditions of such alterations can be peculiar to each polymer. At the transition point, the polymer passes from a soluble state to a visco-elastic state. This phase separation is required for the transition of the polymer from soluble state to fibrous state. For coacervation catalyzed by temperature, the transition temperature of a polymer may be determined by measuring the light scattering of the solution at 300 nm across a time course in which the temperature of the solution is elevated (see, for example Urry and Prasad, U.S. Pat. No. 4,783,523; which is incorporated by reference herein in its entirety). The transition conditions of coacervation catalyzed by parameters such as pH, ionic strength and cation concentration may be determined in a similar manner. For coacervation catalyzed by temperature it is preferable that the polymers of the present invention have a transition temperature of between 20° C. and 40° C. In one embodiment of the invention, the transition temperature of the polymer is reduced upon cross-linking with a transglutaminase. Thus, the transition temperature of the polymer can be adjusted by the number of polypeptides polypeptide monomers capable of being cross-linked by a transglutaminase. As will be appreciated by one skilled in the art, for clinical applications, reduction of the transition temperature at the time of application will facilitate the rapid solidification of the matrix at the wound site.

Transglutaminases, which catalyze the cross-linking of proteins via the formation of $\epsilon$-($\gamma$-glutamyl)lysine isopeptide bonds between protein-bound glutamine and lysine residues, have been isolated from a number of tissue and cell types including epidermis (Floyd and Jetten, *Mol. Cell. Biol.* 9: 4846–4851, 1989), liver (*Biochemistry* 27: 2898–2905, 1988), hair follicle (Wilson et al., *Fed. Proc.* 38: 1809, 1979), keratinocyte (Wilson et al., ibid.; Phillips et al., *Proc. Nat'l Acad. Sci. USA* 87: 9333–9337, 1990), platelets, prostate (described in co-pending, commonly assigned U.S. patent application Ser. Nos. 07/816,284 and 07/998,973) and erythrocytes (Lee et al., *Prep. Biochem.* 16: 321–335, 1986) and from other sources such as from placenta. In a preferred embodiment, the transglutaminase is Factor XIII.

In a related aspect, the present invention provides tissue adhesive kits comprising containers containing a polymer(s) of the present invention, a transglutaminase, and physiologically acceptable diluents and an applicator. The adhesives of the present invention can be provided as lyophilized powders that are reconstituted in a physiologically acceptable diluent (e.g., water for injection, saline, buffered saline or the like) prior to use, or as concentrated or ready-to-use liquids. Within certain embodiments, the applicator is equipped with a syringe, a spray head or an endoscope.

Within one embodiment, the tissue adhesive kit comprises a first container containing a polymer of the present invention, a second container containing an activated transglutaminase, and an applicator. Within another embodiment of the invention, the tissue adhesive kit comprises a first container containing a polymer of the present invention and a non-activated transglutaminase, a second container containing a transglutaminase activator, and an applicator. In kits containing lyophilized powders of concentrated liquids, additional containers containing physiologically acceptable diluents for the polymer and the transglutaminase are included. Those skilled in the art will recognize that certain ingredients can be provided as additional components. For example, a protease inhibitor(s) can be provided in the form of a separate solution that is used as a diluent.

Within certain preferred embodiments, the first and second containers will further contain ingredients, such as inorganic salts, one or more growth factors, stabilizing agents, or solubility enhancers. Suitable solubility enhancers in this regard include sugars, such as mannitol, sorbitol, glucose and sucrose; and surface active agents as disclosed in U.S. Pat. No. 4,909,251. In a preferred embodiment, mannitol is included at 0.5% to 3%, preferably 1%–2%, by weight. Within a preferred embodiment, the transglutaminase is Factor XIII and the kits contain $CaCl_2$. The calcium salt ($CaCl_2$) can be included in the lyophilized formulation or concentrate. In the alternative, a calcium salt is included in the diluent. In any event, the concentration of calcium ions in the final formulation will generally be in the range of 1–15 mM. In cases in which the tissue adhesive kit contains non-activated Factor XIII, the factor XIII formulation is free of catalytic amounts of factor XIII activator.

It is preferred that the tissue adhesive kits be formulated to provide a polymer concentration of between about 5 mg/ml and 100 mg/ml, with concentrations in the range of 35 to 50 mg/ml being particularly preferred.

As noted above, the transglutaminase component of the adhesive kits of the present invention can be a transglutaminase obtained from a variety of tissue and cell sources. Preferred transglutaminases include tissue transglutaminase and prostate transglutaminase. In a particularly preferred embodiment the transglutaminase is factor XIII. The factor XIII suitable for use in the present invention is placental or plasma form of zymogen factor XIII (i.e. factor XIII $a_2$ dimer or $a_2b_2$ tetramer). Bio-equivalent naturally-occurring and genetically engineered forms of the protein can also be used. It is preferred to provide a factor XIII concentration in the final (liquid) adhesive between about 20 $\mu$g/ml and 20 mg/ml, preferably between 50 $\mu$g/ml and 1 mg/ml. Concentrations of factor XIII between 100 and 500 $\mu$g/ml are particularly preferred.

Factor XIII can be isolated from plasma as disclosed in U.S. Pat. Nos. 3,904,751; 3,931,399; 4,597,899 and 4,285,933, incorporated herein by reference, although the use of recombinant factor XIII is preferred in order to minimize or eliminate the use of blood-derived components. Production of recombinant factor XIII is disclosed by Davie et al., EP 268,772 and Grundmann et al., AU-A-69896/87, which are incorporated herein by reference.

It is preferred to prepare factor XIII in the yeast *Saccharomyces cerevisiae* as disclosed in copending U.S. patent application Ser. No. 07/741,263, which is incorporated herein by reference in its entirety. The factor XIII-producing cells are harvested and lysed, and a cleared lysate is prepared. The lysate is fractionated by anion exchange chromatography at neutral to slightly alkaline pH using a column of derivatized agarose, such as diethylaminoethyl anion exchange resin coupled to beaded agarose (e.g, DEAE FAST-FLOW SEPHAROSE, Pharmacia LKB Biotechnology, Piscataway, N.J., or the like). Factor XIII is then precipitated from the column eluate by concentrating the eluate and adjusting the pH to 5.2 to 5.5, such as by diafiltration against ammonium succinate buffer. The precipitate is then dissolved and further purified using conventional chromatographic techniques, such as gel filtration and hydrophobic interaction chromatography.

A suitable factor XIII activator is thrombin. Catalytic amounts of thrombin are those amounts sufficient to induce measurable clotting of a tissue adhesive within a clinically significant time, generally about 1–2 minutes. clotting time is determined by standard assays known in the art. In a typical assay, a 100 $\mu$l sample of fibrinogen in 150 mM NaCl, 10 mM Tris-HCl pH 7.4 is warmed to 37° C., then thrombin or a test sample (100 $\mu$l volume) in 150 mM NaCl, 10 mM Tris-HCl pH 7.4, 10 mM $CaCl_2$ is added. Clotting time is determined with an automatic coagulation timer, such as an ELECTRA 800 coagulation timer (Medical Laboratory Automation, Inc., Pleasantville, N.Y.) or the like. As will be appreciated by those skilled in the art, clotting time will be influenced by such factors as ionic strength, fibrinogen concentration and the presence of additional proteins. In general, the tissue adhesives of the present invention requiring thrombin will contain less than 100 ng/ml thrombin, preferably less than 50 ng/ml. Concentrations of thrombin below about 15 ng/ml are particularly preferred.

The tissue adhesives of the present invention can also contain a growth factor such as PDGF, bFGF, TGF$\alpha$ or EGF. Recombinant growth factors are preferred, and can be prepared as disclosed, for example, in U.S. Pat. Nos. 5,045,633; 5,037,743; 4,783,412 and 4,742,003. A particularly preferred growth factor is PDGF, including native PDGF and its individual component isoforms (AA, BB and AB). Growth factors will generally be included in concentrations of 1–1000 $\mu$g/ml; PDGF is typically included at about 10 to 200 $\mu$g/ml.

The tissue adhesives of the present invention can also include one or more protease inhibitors, such as aprotinin, transexamic acid, alpha-2 plasmin inhibitor, alpha-1 antitrypsin, or the Pittsburgh mutant of alpha-1-antitrypsin (Arg-358 alpha-1-antitrypsin; see Owen et al., *N. Engl. J. Med.* 309: 694–698, 1983 and U.S. Pat. No. 4,711,848) to increase the life span of the adhesive in vivo. Within a preferred embodiment, aprotinin is included in an amount sufficient to provide a final working concentration of 1500–20,000 KIU/ml.

Fibronectin and/or fibronectin fragments can also be included to provide sites for adhesion to cells or other macromolecules. Suitable fragments can be produced by proteolytic digestion of native fibronectin or by recombinant DNA methodology. See, for example, Sekiguchi et al. (*Proc. Natl. Acad. Sci. USA* 77: 2661–2665, 1980), McCarthy et al. (*J. Cell Biol.* 102: 179–188, 1986), Obara et al. (*FEBS Lett.* 213: 261–264, 1987), McCarthy et al. (*Biochemistry* 27: 1380–1388, 1988), U.S. Pat. No. 4,589,881 and U.S. Pat. No. 4,661,111, which are incorporated herein by reference.

The tissue adhesives can be formulated to contain additional proteins, as well as salts, buffering agents and reducing agents. For example, albumin can be included at a concentration between about 1 and 50 mg/ml. Salts, such as NaCl and $CaCl_2$, can be included. Preferred buffers include citrate and phosphate buffers. A preferred reducing agent is ascorbate.

As noted above, the tissue adhesives of the present invention can be prepared as lyophilized powders, liquid concentrates or ready-to-use liquids. Lyophilized powders are preferred for ease of handling and storage.

For kits containing lyophilized or concentrated liquids, a physiologically acceptable diluent is added prior to use, and the components are first solublilzed then mixed to provide a liquid adhesive. To speed dissolution of the lyophilized material, the mixtures can be heated. A magnetic stirring bar or similar device can be included in the first container to facilitate mixing.

For use, the tissue adhesives of the present invention are, if necessary, reconstituted or diluted to the desired final concentration, and an effective amount is applied to the tissue to be sealed. An "effective amount" of tissue adhesive will, in general, be based on the size and nature of the surgical field and can be confirmed by visual examination. Those of skill in the art will recognize an effective amount as that sufficient to cover the wound or joined tissue and form a clotted seal. Effective sealing is recognizable, for example, as a major reduction or cessation of blood or other fluid leakage within about five minutes. Typical amounts used in small skin grafts, ENT surgery and neurosurgery will be in the range of about 1 to 2 ml, and about 5 ml to about 100 ml will be used in thoracic, cardiovascular and trauma surgery and for skin grafting in severe burn cases. The liquid glue is applied to the tissue surface using a syringe equipped with a needle or cannula. For application of the adhesive to large areas (e.g. large skin grafts), the syringe is equipped with a spray head and means for connecting it to a source of sterile propellant gas. Suitable syringes and sprayers are known in the art. The adhesives can also be applied through an endoscope. Following application of the adhesive, the tissues are held in place for about three to five minutes to ensure that the setting adhesive has adhered firmly.

The tissue adhesives of the present invention are useful in sealing a variety of surgical wounds and wounds resulting from trauma, for example, blunt trauma or gunshot wounds to the liver, spleen or kidney. Wounds of this type include those resulting from facial surgery, neurosurgery and ear, nose and throat surgery; skin graft sites; and anastomoses of blood vessels and other hollow organs. In the treatment of anastomoses, the adhesives can be used as a supplement to sutures to seal the edges of the joined tissues around the suture lines. In a similar manner, the adhesives are useful during neurosurgery to seal the edges of sutured dura to prevent leakage of cerebrospinal fluid.

From the foregoing, it will be appreciated that, although specific embodiments of the invention have been described herein for purposes of illustration, various modifications may be made without deviating from the spirit and scope of the invention. Accordingly, the invention is not limited except as by the appended claims.

EXAMPLES

Example 1 Synthesis of test polypeptides substrates

Test polypeptide substrates were designed and synthesized from amino acid sequences suspected of being cross-linked by Factor XIII. Candidate polypeptide sequences from fibrinogen and β-casein were selected and synthesized. Polypeptides were designed and synthesized by systematic deletion of the spacer amino acids between the target glutamine and lysine residues of the fibrinogen polypeptide. Polypeptides were also designed and synthesized by systematic deletion of terminal amino acids of the β-casein polypetide and insertion of a terminal glycine residue as the carboxyl terminal amino acid.

Peptides were synthesized using automated solid phase technology on the ACT 200 and ACT 350 multiple peptide synthesizer (Advanced ChemTech, Louisville K.Y., or the like). Both instruments operate with FMOC strategy using DIC to form activated HOBT esters.

Polypeptides of the present invention were made on the ACT 200 using 1 g of FMOC-Val-WANG resin (Nova Biochem). Following synthesis, the peptide-resin was washed with dimethylformamide followed by a wash with $CH_2Cl_2$. After the washes, the resin was dried. The polypeptide was cleaved from the resin using a TFA solution (0.25 ml $H_2O$, 0.25 ml ethanedithiol, 9.5 ml TFA). The resin was removed from the solution containing the polypeptide by filtering through a fritted glass funnel. The residue was partially dried down under reduced pressure in a rotary evaporator. The residue was precipitated with anhydrous ether, and the precipitate was isolated by filtration on a fritted glass funnel. The precipitate was washed with anhydrous ether and dried in a dessicator under vaccuum. The precipitate is dissolved in Solvent A and a protion of the crude peptide was prepared for HPLC. The purification was performed on a C-18 reverse phase HPLC column (Vydac, Hesperia, Calif.) using a gradient of 0–20% B in 40 minutes (Solvent A: 0.05% trifluoroacetic acid (TFA) in water and Solvent B: 0.05% TFA in 80% acetonitrile, 20% water). Fractions were collected and lyophilized. The molecular mass and amino acid composition were confirmed by mass spectroscopy and amino acid analysis.

Polypeptides of the present invention were also synthesized on the ACT 350 multiple peptide synthesizer (Advanced ChemTech, Louisville K.Y., or the like). Each peptide was made on a 50 mg resin scale using FMOC-Val-Wang resin (Advanced ChemTech). The synthesis conditions were similar to the synthesis described above, with the exception that the final washes are DMF and $CH_2Cl_2$/ $CH_3OH$ (1:1 vol/vol). The polypeptide was cleaved from the resin as described above. Purification of the peptide was performed on a C-18 column (Vydac, Hesperia, Calif., or the like) using a gradient of 0–40% B in from 5 to 35 minutes. The molecular masses and amino acid compositions were confirmed by mass spectroscopy and amino acid analysis.

Example 2 Cross-linking assays

The ability of the test polypeptides to form Factor XIII-induced multimers, and the susceptibility of the polypeptides to deamidation were assessed using the method described in detail below.

Approximately 0.5 mg of lyophilized polypeptide was dissolved in 50 mM Tris, 125 mM NaCl (pH 7.6) to give a final concentration of 2 mM by weight. Where necessary, the pH of the solution was adjusted to 7.6 with 0.1N NaOH. Each test polypeptide solution received 50 mM $CaCl_2$ to a final concentration of 2.5 mM. For each reaction, a negative control lacking Factor XIII was included. A positive control of the fibrinogen polypeptide Thr-Ile-Gly-Glu-Gly-Gln-Gln-His-His-Leu-Gly-Gly-Ala-Lys-Gln-Ala-Gly-Asp-Val was used for each set of reactions. The reactions were initiated by the addition of 40 µg/ml of recombinant Factor XIII followed by 0.1 unit of bovine thrombin (Enzyme Research Laboratories, Inc.) to each solution, except the negative controls. The reactions were incubated in a 37° C. water bath. Samples of 10 µl were taken from each reaction at 0 minutes, 30 minutes, 60 minutes, 120 minutes and overnight. The reactions were stopped by boiling for one minutes. The samples were diluted to 50 µl TBS buffer (120 mM NaCl, 50 mM Tris (pH 7.6)), and the samples were prepared for HPLC analysis.

Each reaction was chromatographed on a C-18 reverse phase HPLC column (Vydac, Hesperia, Calif., or the like) using a gradient of 0–40% B in 30 minutes (solvent A: 0.05% TFA in water and Solvent B: 0.045% TFA in 80% acetonitrile/20% water) on a Hewlett Packard 1090 Series II HPLC. The signal was detected at a wavelength of 215 nm. The area % of each reaction product was collected and plotted versus time to determine the rates of polypeptide utilization and dimer formation. A deamidation ratio was determined by dividing the deamidation rate by the dimerization rate. Suitable polypeptides showed a fast rate of substrate utilization, a fast rate of dimer formation and a low deamidation ratio relative to the fibrinogen polypeptide control. Table 1 shows the results of cross-linking assays for selected polypeptide substrates. The abbreviations used in Table 1 are as follows: d[S]/dt indicates the rate of substrate utilization, d[$S_2$]/dt indicates the rate of dimer formation and (-$NH_2/S_2$) indicates the relative rates of deamidation to dimerization. The initial rates were normalized to that of the fibrinogen polypeptide Thr-Ile-Gly-Glu-Gly-Gln-Gln-His-His-Leu-Gly-Gly-Ala-Lys-Gln-Ala-Gly-Asp-Val.

TABLE 1

Rates of fRXIIIa Crosslinking of Truncated Frbrinogen Peptides

| Sequence | Initial rates given in uM (monomer)/min | | | |
|---|---|---|---|---|
| | Monomer Consumption d[S]/dt | Hydrolysis d[-NH3]/dt | Crosslinking d(2[S-])/dt | Hydrolysis % |
| TIGEGQQHHLGGAKQAGDV | −20.0 | 5.2 | 16.4 | 24 |
| TIGEGQ_HHLGGAKQAGDV (-Q) | −12.8 | 0.6 | 11.4 | 5 |
| _IGEGQ_HHLGGAKQAGD_ | −12.5 | −1.4 | 14.1 | 0 |
| _GEGQ_HHLGGAKQAG_ | −13.1 | 0.4 | 11.2 | 3 |
| _EGQ_HHLGGAKQA_ | −10.8 | 0.0 | 9.8 | 0 |
| _GQ_HHLGGAKQ_ (-Q,G) | −6.9 | 0.0 | 6.2 | 0 |
| TIGEGQ_HHLG_AKQAGDV | −7.0 | 3.0 | 4.0 | 43 |
| _GQ_HHLG_AKQ_ (-Q,Q) | −4.7 | 0.0 | 4.9 | 0 |
| TIGEGQ_HHLGGAK_AGDV | −10.0 | 1.4 | 8.8 | 14 |
| _GQ_HHLGGAK_A_ (-Q,G,Q) | −2.4 | 0.8 | 1.8 | 31 |
| TIGEGQ_HHL_GAKQAGDV | −8.4 | 5.4 | 3.6 | 60 |
| _EGQ_HHL_GAKQAG_ | −6.0 | 5.4 | 3.0 | 64 |
| _GQ_HHL_GAKQA_ | −8.4 | −0.2 | 8.4 | 0 |
| flanked variants | | | | |
| VPGVGGQ_HHLGGAKQVPGVG | −12.8 | 0.0 | 11.8 | 0 |
| GVGVPGQ_HHLGGAKQGVGVP | −7.3 | 1.7 | 5.6 | 23 |
| GQ_HHLGGAKQG | −4.4 | 0.0 | 4.4 | 0 |
| VGQ_HHLGGAKVPG | −18.0 | 0.0 | 16.2 | 0 |
| VPGVGQ_HHLGGAKVPGVG | −20.8 | 1.8 | 15.8 | 10 |
| VGGQ_HHLGGAKQVPG | 11.0 | 0.0 | 11.0 | 0 |
| GVGGQ_HHLGGAKQVP | −9.8 | 0.0 | 7.6 | 0 |
| Casein-derived peptides | | | | |
| LSQSKVG | −5.2 | 1.2 | 6.8 | 15 |
| VPGVGLSQSKVGVPGVG | −32.0 | 12.5 | 15.0 | 45 |

*hydrolysis may also be refered to as deamidation
Reaction Conditions:
2mM [substrate]; 40 ug/ml [rFXIIIa]; 2.0 U/ml [Thrombin]; 2.5 mM [CaCl2]; 125 mM [NaCl]; 50 mM [Tris-HCl]; pH 7.4
The rFXIIIa was preactivated prior to mixing with substrate.
  Reaction rates are given as the rate of monomer incorporation into dimers.

The amino acid sequence in Table 1 uses the generally accepted one-letter code for amino acid residues.

The overnight sample for each reaction was subjected to HPLC-Mass Spectroscopy using a PE SCIEX API III system (Perkin Elmer Sciex Instruments, Thornhill, Ontario, Canada) in combination with a Waters 625 LC (Waters Chromatography, Milford, Mass.) system equipped with an autosampler to identify the molecular masses of the species present in each reaction.

The overnight samples prepared as described above were collected and arranged into batches. Each batch of samples was preceded by a 0.1M acetic acid indicator sample and followed by the fibrinogen peptide control Thr-Ile-Gly-Glu-Gly-Gln-Gln-His-His-Leu-Gly-Gly-Ala-Lys-Gln-Ala-Gly-Asp-Val. The batches were chromatographed on a C-18 reverse phase column (2.1×150 mm, 5μ, 300 angstrom; Vydac Hesperia, Calif., or the like) using a gradient of 0–50% B in 30 minutes (solvent A: 0.05% TFA in water and Solvent B: 0.045% TFA in 80% acetonitrile/20% water) on the Waters LC (Waters Chromatography) system equipped with an autosampler programmed to deliver 20 μl of each sample. The flow from the HPLC was split approximately 10:1 via the SCIEX splitter with the smaller volume being directed (at approximately 20 μl/min) into the mass analyzer and the remainder of the flow directed back to the HPLC UV detector in the Waters LC. This arrangement created a short, consistent (approximately 0.3 min) delay between the mass determination and the UV absorbance detection due to the length of the path traveled by the flow to the UV detector. The signal was detected by the UV detector at a wavelength of 215 nm. The molecular mass of each component in the HPLC peaks was determined by the PE SCIEX API III Mass Analyzer (IonSpray source with triple quaprapole resolution) that had been calibrated with a polypropylene glycol mw 1000 solution (Aldrich Chemical Company Inc., Milwaukee, Wis.) designating the following m/z (mass to charge rations):

59.000
520.395
906.673
1254.92
1545.133
1836.342
2010.468

The PE SCIEX API III was programmed to the following parameters:

| DACs SETTINGS | |
|---|---|
| ISV | 5500.00 |
| IN | 650.00 |
| OR | 65.00 |
| RO | 30.00 |
| M1 | 1000.00 |
| RE1 | 120.00 |
| DM1 | 0.09 |
| R1 | 27.00 |
| L7 | −50.00 |
| R2 | −50.00 |
| M3 | 1000.00 |
| RE3 | 122.00 |
| DM3 | 0.09 |
| R3 | −75.00 |
| L9 | −250.00 |
| FP | −250.00 |
| MU | −4200.00 |

| On/Offs SETTINGS | |
|---|---|
| CC | 1 |
| CG | Off |

| ADCs SETTINGS | |
|---|---|
| DIμA | −0.20 |
| CGT | −1.53 |
| ISv | 4.89 |
| UV | −24.43 |

The mass data generated from each peak was interpreted to identify the molecular species present from each peak.

From the foregoing, it will be appreciated that, although specific embodiments of the invention have been described herein for purposes of illustration, various modifications can be made without deviating from the spirit and scope of the invention. Accordingly, the invention is not limited except as by the appended claims.

We claim:

1. A polypeptide of from about 9–120 amino acid residues comprising a segment of the formula $S_1$-Y-$S_2$, wherein:
   $S_1$ is selected from the group consisting of Ile-Gly-Glu-Gly-Gln (SEQ ID NO:1), Gly-Glu-Gly-Gln (SEQ ID NO:2), Glu-Gly-Gln (SEQ ID NO:3), and Gly-Gln (SEQ ID NO:4);
   Y is His-His-Leu-Gly-Gly (SEQ ID NO:5) or His-His-Leu-Gly (SEQ ID NO:6); and
   $S_2$ is selected from the group consisting of Ala-Lys-Gln-Ala-Gly-Asp (SEQ ID NO:7), Ala-Lys-Gln-Ala-Gly (SEQ ID NO:8), Ala-Lys-Gln-Ala (SEQ ID NO:9), Ala-Lys-Gln (SEQ ID NO:10), Ala-Lys-Ala-Gly-Asp-Val (SEQ ID NO:11), Ala-Lys-Ala (SEQ ID NO:12) and Ala-Lys (SEQ ID NO:13), wherein the polypeptide has an amino-terminus and a carboxy-terminus and is cross-linkable by a transglutaminase.

2. A polypeptide according to claim 1, wherein the polypeptide is flanked on either or both the amino-terminus and the carboxy-terminus by an elastomeric polypeptide.

3. A polypeptide according to claim 2, wherein the elastomeric polypeptide is a pentapeptide or a tetrapeptide.

4. A polypeptide according to claim 2, wherein the elastomeric polypeptide is Val-Pro-Gly-Val-Gly (SEQ ID NO:15), Ala-Pro-Gly-Val-Gly (SEQ ID NO:16), Gly-Val-Gly-Val-Pro (SEQ ID NO:17), Val-Pro-Gly-Gly (SEQ ID NO:18) or any portion thereof.

5. A polypeptide according to claim 2, wherein the resultant amino-terminus of the polypeptide is Val and the carboxy-terminus of the polypeptide is Gly.

6. A polypeptide according to claim 1, wherein the transglutaminase is Factor XIII.

7. A polypeptide according to claim 1, wherein the polypeptide is Gly-Gln-His-His-Leu-Gly-Gly-Ala-Lys-Gln (SEQ ID NO:14).

8. A biocompatible, bioadhesive, transglutaminase cross-linkable copolymer which comprises:
   a) a first polypeptide monomer wherein the first polypeptide monomer is a polypeptide of from about 9–120 amino acid residues comprising a segment of the formula $S_1$-Y-$S_2$, wherein:
      $S_1$ is selected from the group consisting of Ile-Gly-Glu-Gly-Gln (SEQ ID NO:1), Gly-Glu-Gly-Gln (SEQ ID NO:2), Glu-Gly-Gln (SEQ ID NO:3), and Gly-Gln (SEQ ID NO:4);
      Y is His-His-Leu-Gly-Gly (SEQ ID NO:5) or His-His-Leu-Gly (SEQ ID NO:6); and
      $S_2$ is selected from the group consisting of Ala-Lys-Gln-Ala-Gly-Asp (SEQ ID NO:7), Ala-Lys-Gln-Ala-Gly (SEQ ID NO:8), Ala-Lys-Gln-Ala (SEQ ID NO:9), Ala-Lys-Gln (SEQ ID NO:10), Ala-Lys-Ala-Gly-Asp-Val (SEQ ID NO:11), Ala-Lys-Ala (SEQ ID NO:12) and Ala-Lys (SEQ ID NO:13), wherein the first polypeptide monomer has an amino-terminus and a carboxy-terminus and is cross-linkable by a transglutaminase; and
   b) a second polypeptide monomer comprising a polypeptide capable of being non-enzymatically polymerized into soluble, biocompatible, bioadhesive polymers.

9. A biocompatible, bioadhesive, transglutaminase cross-linkable copolymer according to claim 8, wherein the first polypeptide monomer is flanked on either or both the amino-terminus and the carboxy-terminus by an elastomeric polypeptide.

10. A biocompatible, bioadhesive, transglutaminase cross-linkable copolymer according to claim 9, wherein the elastomeric polypeptide is a pentapeptide or a tetrapeptide.

11. A biocompatible, bioadhesive, transglutaminase cross-linkable copolymer according to claim 9, wherein the elastomeric polypeptide is Val-Pro-Gly-Val-Gly (SEQ ID NO:15), Ala-Pro-Gly-Val-Gly (SEQ ID NO:16), Gly-Val-Gly-Val-Pro (SEQ ID NO:17), Val-Pro-Gly-Gly (SEQ ID NO:18) or any portion thereof.

12. A biocompatible, bioadhesive, transglutaminase cross-linkable copolymer according to claim 9 wherein the amino-terminus of the first polypeptide monomer is Val and the carboxy-terminus of the first polypeptide monomer is Gly.

13. A biocompatible, bioadhesive, transglutaminase cross-linkable copolymer according to claim 8, wherein the transglutaminase is Factor XIII.

14. A biocompatible, bioadhesive, transglutaminase cross-linkable copolymer of claim 8, wherein the second polypeptide monomer is Val-Pro-Gly-Val-Gly (SEQ ID NO:15), Ala-Pro-Gly-Val-Gly (SEQ ID NO:16), Gly Val Gly Val Pro (SEQ ID NO:17) Val-Pro-Gly-Gly (SEQ ID NO:18).

15. A biocompatible, transglutaminase cross-linkable homopolymer which comprises polypeptide monomers of from about 9–120 amino acid residues comprising a segment of the formula $S_1$-Y-$S_2$, wherein:
   $S_1$ is selected from the group consisting of Ile-Gly-Glu-Gly-Gln (SEQ ID NO:1), Gly-Glu-Gly-Gln (SEQ ID NO:2), Glu-Gly-Gln (SEQ ID NO:3), and Gly-Gln (SEQ ID NO:4);
   Y is His-His-Leu-Gly-Gly (SEQ ID NO:5) or His-His-Leu-Gly (SEQ ID NO:6);
   $S_2$ is selected from the group consisting of Ala-Lys-Gln-Ala-Gly-Asp (SEQ ID NO:7), Ala-Lys-Gln-Ala-Gly (SEQ ID NO:8), Ala-Lys-Gln-Ala (SEQ ID NO:9), Ala-Lys-Gln (SEQ ID NO:10), Ala-Lys-Ala-Gly-Asp-Val (SEQ ID NO:11), Ala-Lys-Ala (SEQ ID NO:12) and Ala-Lys (SEQ ID NO:13), wherein the polypeptide monomers have an amino-terminus and a carboxy-terminus and are cross-linkable by a transglutaminase.

16. A biocompatible, transglutaminase cross-linkable homopolymer according to claim 15, wherein the polypeptide monomer is flanked on either or both the amino-terminus and the carboxy-terminus by an elastomeric polypeptide.

17. A biocompatible, transglutaminase cross-linkable homopolymer according to claim 16, wherein the elastomeric polypeptide is a pentapeptide or a tetrapeptide.

18. A biocompatible, transglutaminase cross-linkable homopolymer according to claim 16, wherein the elastomeric polypeptide is Val-Pro-Gly-Val-Gly (SEQ ID NO:15), Ala-Pro-Gly-Val-Gly (SEQ ID NO:16), Gly-Val-Gly-Val-Pro (SEQ ID NO:17), Val-Pro-Gly-Gly (SEQ ID NO:18) or any portion thereof.

19. A biocompatible, transglutaminase cross-linkable homopolymer according to claim 16, wherein the amino-terminus of the polypeptide monomer is Val and the carboxy-terminus of the polypeptide monomer is Gly.

20. A biocompatible, transglutaminase cross-linkable homopolymer according to claim 15, wherein the transglutaminase is Factor XIII.

21. A tissue adhesive kit comprising:
a first container containing a biocompatible, bioadhesive, transglutaminase cross-linkable copolymer which comprises:
a) a first polypeptide monomer wherein the first polypetide monomer is a polypeptide of from about 9–120 amino acid residues comprising a segment of the formula $S_1$-Y-$S_2$, wherein:
$S_1$ is selected from the group consisting of Ile-Gly-Glu-Gly-Gln (SEQ ID NO:1), Gly-Glu-Gly-Gln (SEQ ID NO:2), Glu-Gly-Gln (SEQ ID NO:3), and Gly-Gln (SEQ ID NO:4);
Y is His-His-Leu-Gly-Gly (SEQ ID NO:5) or His-His-Leu-Gly (SEQ ID NO:6); and
$S_2$ is selected from the group consisting of Ala-Lys-Gln-Ala-Gly-Asp (SEQ ID NO:7), Ala-Lys-Gln-Ala-Gly (SEQ ID NO:8), Ala-Lys-Gln-Ala (SEQ ID NO:9), Ala-Lys-Gln (SEQ ID NO:10), Ala-Lys-Ala-Gly-Asp-Val (SEQ ID NO:11), Ala-Lys-Ala (SEQ ID NO:12) and Ala-Lys (SEQ ID NO:13), wherein the first polypeptide monomer has an amino-terminus and a carboxy-terminus and is cross-linkable by a transglutaminase; and
b) a second polypeptide monomer comprising a polypeptide capable of being non-enzymatically polymerized into soluble, biocompatible, bioadhesive polymers; and
a second container containing an activated transglutaminase.

22. A tissue adhesive kit according to claim 21, wherein the transglutaminase is factor XIII.

23. A tissue adhesive kit according to claim 21, wherein the first polypeptide monomer is flanked on either or both the amino-terminus and the carboxy-terminus by an elastomeric polypeptide.

24. A tissue adhesive kit according to claim 23, wherein the elastomeric polypeptide is a pentapeptide or a tetrapeptide.

25. A tissue adhesive kit according to claim 23, wherein the elastomeric polypeptide is Val-Pro-Gly-Val-Gly (SEQ ID NO:15), Ala-Pro-Gly-Val-Gly (SEQ ID NO:16), Gly-Val-Gly-Val-Pro (SEQ ID NO:17), Val-Pro-Gly-Gly (SEQ ID NO:18) or any portion thereof.

26. A tissue adhesive kit according to claim 23, wherein the amino-terminus of the first polypeptide monomer is Val and the carboxy-terminus of the first polypeptide monomer is Gly.

27. A tissue adhesive kit according to claim 21, wherein the contents of the first and second containers are in the form of a lyophilized powder or a liquid concentrate and wherein the kit further comprises a third container containing a physiologically acceptable diluent.

28. A tissue adhesive kit according to claim 21, wherein the kit further comprises an applicator.

29. A tissue adhesive kit comprising:
a first container containing a non-activated transglutaminase and a biocompatible, bioadhesive, transglutaminase cross-linkable copolymer which comprises:
a) a first polypeptide monomer wherein the first polypetide monomer is a polypeptide of from about 9–120 amino acid residues comprising a segment of the formula $S_1$-Y-$S_2$, wherein:
$S_1$ is selected from the group consisting of Ile-Gly-Glu-Gly-Gln (SEQ ID NO:1), Gly-Glu-Gly-Gln (SEQ ID NO:2), Glu-Gly-Gln (SEQ ID NO:3), and Gly-Gln (SEQ ID NO:4);
Y is His-His-Leu-Gly-Gly (SEQ ID NO:5) or His-His-Leu-Gly (SEQ ID NO:6); and
$S_2$ is selected from the group consisting of Ala-Lys-Gln-Ala-Gly-Asp (SEQ ID NO:7), Ala-Lys-Gln-Ala-Gly (SEQ ID NO:8), Ala-Lys-Gln-Ala (SEQ ID NO:9), Ala-Lys-Gln (SEQ ID NO:10), Ala-Lys-Ala-Gly-Asp-Val (SEQ ID NO:11), Ala-Lys-Ala (SEQ ID NO:12) and Ala-Lys (SEQ ID NO:13), wherein the first polypeptide monomer has an amino-terminus and a carboxy-terminus and is cross-linkable by a transglutaminase; and
b) a second polypeptide monomer comprising a polypeptide capable of being non-enzymatically polymerized into soluble, biocompatible, bioadhesive polymers; and
a second container containing a transglutaminase activator.

30. A tissue adhesive kit according to claim 29, wherein the transglutaminase is factor XIII.

31. A tissue adhesive kit according to claim 29, wherein the first polypeptide monomer is flanked on either or both the amino-terminus and the carboxy-terminus by an elastomeric polypeptide.

32. A tissue adhesive kit according to claim 31, wherein the elastomeric polypeptide is a pentapeptide or a tetrapeptide.

33. A tissue adhesive kit according to claim 31, wherein the elastomeric polypeptide is Val-Pro-Gly-Val-Gly (SEQ ID NO:15), Ala-Pro-Gly-Val-Gly (SEQ ID NO:16), Gly-Val-Gly-Val-Pro (SEQ ID NO:17), Val-Pro-Gly-Gly (SEQ ID NO:18) or any portion thereof.

34. A tissue adhesive kit according to claim 31, wherein the amino-terminus of the first polypeptide monomer is Val and the carboxy-terminus of the first polypeptide monomer is Gly.

35. A tissue adhesive kit according to claim 29, wherein the transglutaminase activator is thrombin.

36. A tissue adhesive kit according to claim 29, wherein the contents of the first and second containers are in the form of a lyophilized powder or a liquid concentrate and wherein the kit further comprises a third container containing a physiologically acceptable diluent.

37. A tissue adhesive kit according to claim 29, wherein the kit further comprises an applicator.

38. A tissue adhesive kit comprising:
a first container containing a biocompatible, transglutaminase cross-linkable homopolymer which comprises polypeptide monomers of from about 9–120 amino acid residues comprising a segment of the formula $S_1$-Y-$S_2$, wherein:
$S_1$ is selected from the group consisting of Ile-Gly-Glu-Gly-Gln (SEQ ID NO:1), Gly-Glu-Gly-Gln (SEQ ID NO:2), Glu-Gly-Gln (SEQ ID NO:3), and Gly-Gln (SEQ ID NO:4);
Y is His-His-Leu-Gly-Gly (SEQ ID NO:5) or His-His-Leu-Gly (SEQ ID NO:6); and
$S_2$ is selected from the group consisting of Ala-Lys-Gln-Ala-Gly-Asp (SEQ ID NO:7), Ala-Lys-Gln-Ala-Gly (SEQ ID NO:8), Ala-Lys-Gln-Ala (SEQ ID NO:9), Ala-Lys-Gln (SEQ ID NO:10), Ala-Lys-Ala-Gly-Asp-Val (SEQ ID NO:11), Ala-Lys-Ala (SEQ ID NO:12) and Ala-Lys (SEQ ID NO:13),
wherein the polypeptide monomers have an amino-terminus and a carboxy-terminus and are cross-linkable by a transglutaminase; and a second container containing an activated transglutaminase.

39. A tissue adhesive kit according to claim 38, wherein the polypeptide monomer is flanked on either or both the amino-terminus and the carboxy-terminus by an elastomeric polypeptide.

40. A tissue adhesive kit according to claim 39, wherein the elastomeric polypeptide is a pentapeptide or a tetrapeptide.

41. A tissue adhesive kit according to claim 39, wherein the elastomeric polypeptide is Val-Pro-Gly-Val-Gly (SEQ ID NO:15), Ala-Pro-Gly-Val-Gly (SEQ ID NO:16), Gly-Val-Gly-Val-Pro (SEQ ID NO:17), Val-Pro-Gly-Gly (SEQ ID NO:18) or any portion thereof.

42. A tissue adhesive kit according to claim 39, wherein the amino-terminus of the polypeptide monomer is Val and the carboxy-terminus of the polypeptide monomer is Gly.

43. A tissue adhesive kit according to claim 38, wherein the transglutaminase is factor XIII.

44. A tissue adhesive kit according to claim 38, wherein the contents of the first and second containers are in the form of a lyophilized powder or a liquid concentrate and wherein the kit further comprises a third container containing a physiologically acceptable diluent.

45. A tissue adhesive kit according to claim 38, wherein the kit further comprises an applicator.

46. A tissue adhesive kit comprising:
   a first container containing a non-activated transglutaminase and a biocompatible, transglutaminase cross-linkable homopolymer which comprises polypeptide monomers of from about 9–120 amino acid residues comprising a segment of the formula $S_1$-Y-$S_2$, wherein:
      $S_1$ is selected from the group consisting of Ile-Gly-Glu-Gly-Gln (SEQ ID NO:1), Gly-Glu-Gly-Gln (SEQ ID NO:2), Glu-Gly-Gln (SEQ ID NO:3), and Gly-Gln (SEQ ID NO:4);
      Y is His-His-Leu-Gly-Gly (SEQ ID NO:5) or His-His-Leu-Gly (SEQ ID NO:6); and
      $S_2$ is selected from the group consisting of Ala-Lys-Gln-Ala-Gly-Asp (SEQ ID NO:7), Ala-Lys-Gln-Ala-Gly (SEQ ID NO:8), Ala-Lys-Gln-Ala (SEQ ID NO:9), Ala-Lys-Gln (SEQ ID NO:10), Ala-Lys-Ala-Gly-Asp-Val (SEQ ID NO:11), Ala-Lys-Ala (SEQ ID NO:12) and Ala-Lys (SEQ ID NO:13),
      wherein the polypeptide monomers have an amino-terminus and a carboxy-terminus and are cross-linkable by a transglutaminase; and
   a second container containing a transglutaminase activator.

47. A tissue adhesive kit according to claim 46, wherein the polypeptide monomer is flanked on either or both the amino-terminus and the carboxy-terminus by an elastomeric polypeptide.

48. A tissue adhesive kit according to claim 47, wherein the elastomeric polypeptide is a pentapeptide or a tetrapeptide.

49. A tissue adhesive kit according to claim 47, wherein the elastomeric polypeptide is Val-Pro-Gly-Val-Gly (SEQ ID NO:15), Ala-Pro-Gly-Val-Gly (SEQ ID NO:16), Gly-Val-Gly-Val-Pro (SEQ ID NO:17), Val-Pro-Gly-Gly (SEQ ID NO:18) or any portion thereof.

50. A tissue adhesive kit according to claim 47, wherein the amino-terminus of the polypeptide monomer is Val and the carboxy-terminus of the polypeptide monomer is Gly.

51. A tissue adhesive kit according to claim 47, wherein the transglutaminase is factor XIII.

52. A tissue adhesive kit according to claim 47, wherein the transglutaminase activator is thrombin.

53. A tissue adhesive kit according to claim 47, wherein the contents of the first and second containers are in the form of a lyophilized powder or a liquid concentrate and wherein the kit further comprises a third container containing a physiologically acceptable diluent.

54. A tissue adhesive kit according to claim 47, wherein the kit further comprises an applicator.

* * * * *

SEQUENCE LISTING (1) GENERAL INFORMATION:

(iii) NUMBER OF SEQUENCES: 18

(2) INFORMATION FOR SEQ ID NO:1:

(i) SEQUENCE CHARACTERISTICS:
      (A) LENGTH: 5 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO:1:

Ile Gly Glu Gly Gln
1               5

(2) INFORMATION FOR SEQ ID NO:2:

(i) SEQUENCE CHARACTERISTICS:
      (A) LENGTH: 4 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO:2:

Gly Glu Gly Gln
1

(2) INFORMATION FOR SEQ ID NO:3:

(i) SEQUENCE CHARACTERISTICS:
      (A) LENGTH: 3 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO:3:

Glu Gly Gln (2) INFORMATION FOR SEQ ID NO:4:

(i) SEQUENCE CHARACTERISTICS:
        (A) LENGTH: 2 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:4:

Gly Gln
1

(2) INFORMATION FOR SEQ ID NO:5:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:5:

His His Leu Gly Gly
1           5

(2) INFORMATION FOR SEQ ID NO:6:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:6:

His His Leu Gly
1

(2) INFORMATION FOR SEQ ID NO:7:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:7:

Ala Lys Gln Ala Gly Asp
1           5

(2) INFORMATION FOR SEQ ID NO:8:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:8:

Ala Lys Gln Ala Gly

```
1               5
```

(2) INFORMATION FOR SEQ ID NO:9:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:9:

```
Ala Lys Gln Ala
1
```

(2) INFORMATION FOR SEQ ID NO:10:

(i) SEQUENCE CHARACTERISTICS:
        (A) LENGTH: 3 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:10:

```
Ala Lys Gln
1
```

(2) INFORMATION FOR SEQ ID NO:11:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:11:

```
Ala Lys Ala Gly Asn Val
1               5
```

(2) INFORMATION FOR SEQ ID NO:12:

(i) SEQUENCE CHARACTERISTICS:
        (A) LENGTH: 3 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:12:

```
Ala Lys Ala
1
```

(2) INFORMATION FOR SEQ ID NO:13:

(i) SEQUENCE CHARACTERISTICS:
        (A) LENGTH: 2 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:13:

```
Ala Lys
```

(2) INFORMATION FOR SEQ ID NO:14:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:14:

Gly Gln His His Leu Gly Gly Ala Lys Gln
1               5                   10

(2) INFORMATION FOR SEQ ID NO:15:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:15:

Val Pro Gly Val Gly
1               5

(2) INFORMATION FOR SEQ ID NO:16:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:16:

Ala Pro Gly Val Gly
1               5

(2) INFORMATION FOR SEQ ID NO:17:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:17:

Gly Val Gly Val Pro
1               5

(2) INFORMATION FOR SEQ ID NO:18:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:18:

Val Pro Gly Gly